(12) United States Patent
Kawaguchi et al.

(10) Patent No.: US 11,377,685 B2
(45) Date of Patent: Jul. 5, 2022

(54) BASE SEQUENCE DETERMINATION APPARATUS, CAPILLARY ARRAY ELECTROPHORESIS APPARATUS, AND METHOD

(71) Applicant: HITACHI HIGH-TECH CORPORATION, Tokyo (JP)

(72) Inventors: Yohei Kawaguchi, Tokyo (JP); Tomohiro Yasuda, Tokyo (JP); George Chalkidis, Tokyo (JP); Takahide Yokoi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 318 days.

(21) Appl. No.: 16/071,956

(22) PCT Filed: Jan. 28, 2016

(86) PCT No.: PCT/JP2016/052495
§ 371 (c)(1),
(2) Date: Jul. 23, 2018

(87) PCT Pub. No.: WO2017/130349
PCT Pub. Date: Aug. 3, 2017

(65) Prior Publication Data
US 2019/0032126 A1 Jan. 31, 2019

(51) Int. Cl.
*G16B 30/00* (2019.01)
*C12Q 1/6869* (2018.01)
(Continued)

(52) U.S. Cl.
CPC ........... *C12Q 1/6869* (2013.01); *C12N 15/09* (2013.01); *C12Q 1/68* (2013.01);
(Continued)

(58) Field of Classification Search
None
See application file for complete search history.

(56) References Cited

U.S. PATENT DOCUMENTS

2008/0183164 A1* 7/2008 Elkins .................... A61B 18/02
606/21
2010/0089771 A1 4/2010 Utsunomiya et al.
(Continued)

FOREIGN PATENT DOCUMENTS

WO 2008/050426 A1 5/2008

OTHER PUBLICATIONS

International Search Report issued for WO 2017/130349 A1, dated Apr. 12, 2016.

*Primary Examiner* — Robert T. Crow
(74) *Attorney, Agent, or Firm* — Volpe Koenig

(57) ABSTRACT

A base sequence determination apparatus includes (1) a mobility correction unit that outputs a mobility correction signal obtained by mobility correction of a time-series signal of a wavelength spectrum corresponding to each base, (2) a deconvolution unit that executes processes for calculating a deconvoluted signal of the mobility correction signal respectively for a plurality of parameter candidates of point spread function, calculating variance of peak intervals for the calculated deconvoluted signal, specifying a parameter of the point spread function using the calculated variance, and outputting the deconvoluted signal corresponding to the point spread function having the specified parameter as an updated deconvoluted signal, (3) a peak extracting unit that extracts a peak waveform from the updated deconvoluted signal and outputs an updated peak-extracted signal, and (4) a sequence specifying unit that inputs the updated peak-extracted signal and determines a base sequence.

8 Claims, 8 Drawing Sheets

(51) Int. Cl.
*C12N 15/09* (2006.01)
*C12Q 1/68* (2018.01)
*G01N 27/447* (2006.01)
*B01L 3/00* (2006.01)

(52) U.S. Cl.
CPC ....... *G01N 27/44726* (2013.01); *G16B 30/00* (2019.02); *B01L 3/00* (2013.01); *B01L 3/5027* (2013.01); *C12Q 2565/125* (2013.01)

(56) References Cited

U.S. PATENT DOCUMENTS

| | | | | |
|---|---|---|---|---|
| 2010/0266177 | A1* | 10/2010 | Zhang | G06K 9/00503 382/129 |
| 2010/0292102 | A1* | 11/2010 | Nouri | G16B 50/40 506/16 |
| 2012/0173159 | A1* | 7/2012 | Davey | G16B 30/10 702/20 |
| 2014/0153058 | A1* | 6/2014 | Lovette | H04N 1/00063 358/406 |

* cited by examiner

[Fig. 1]
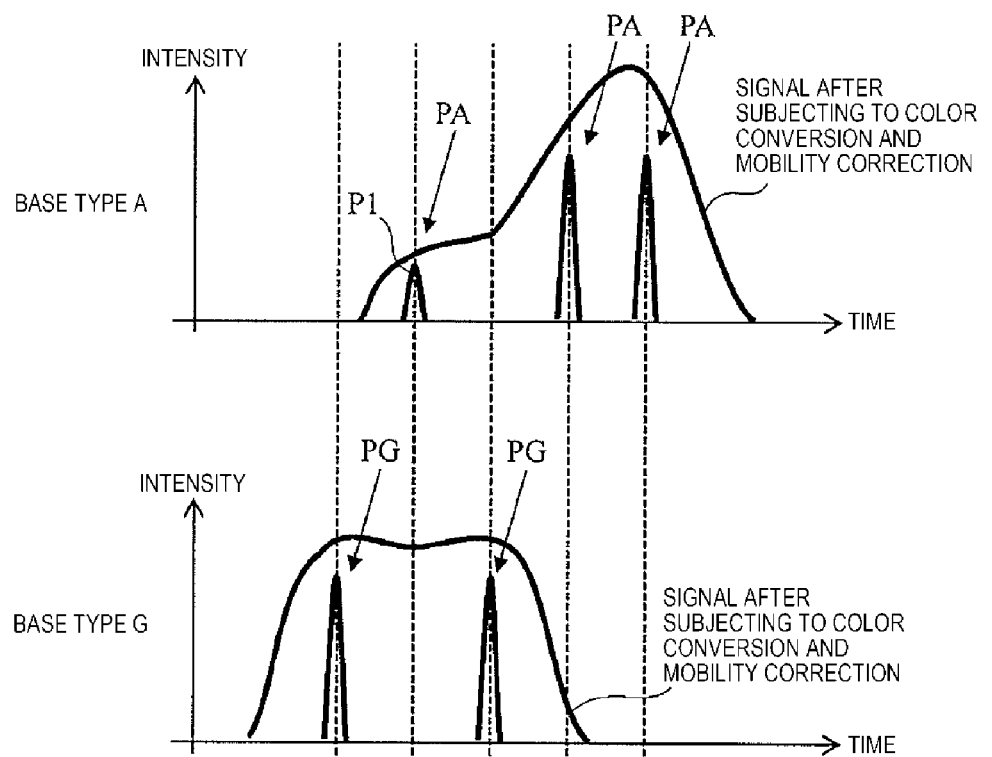

[Fig. 2]
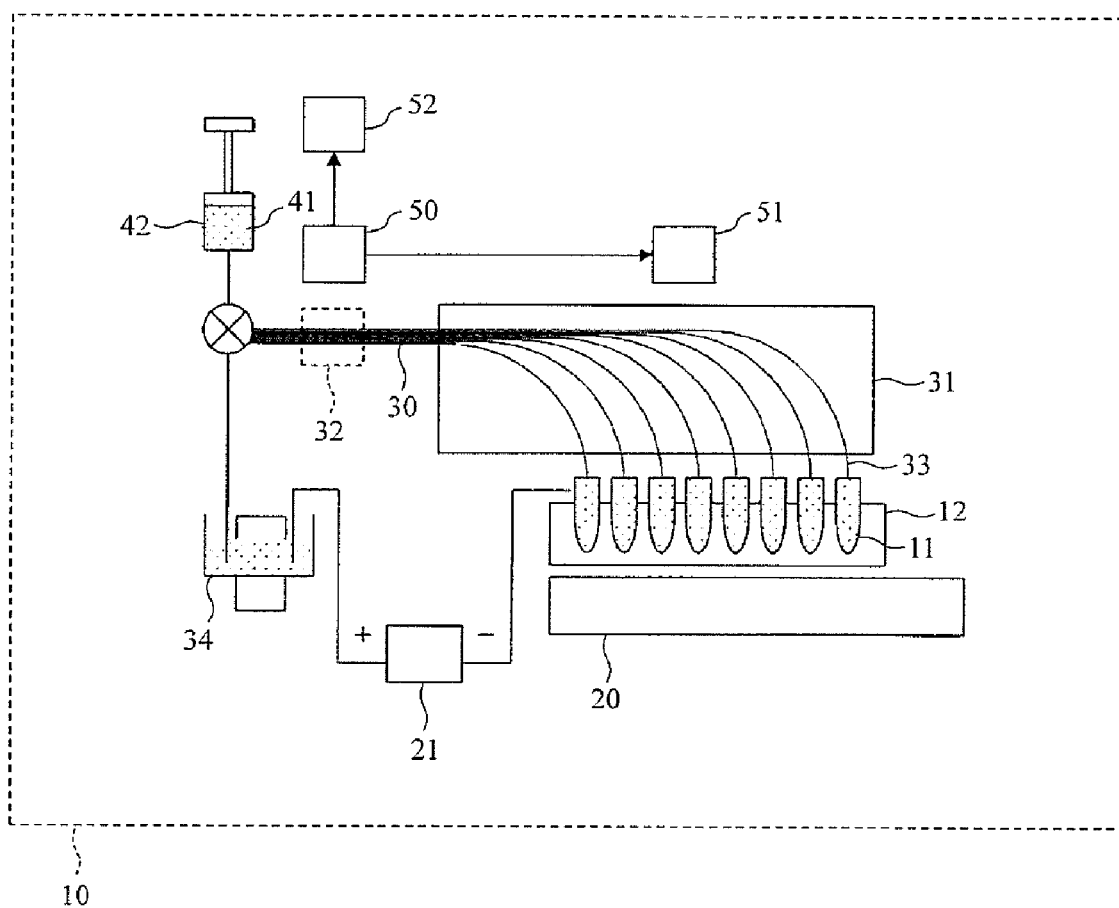

[Fig. 3]
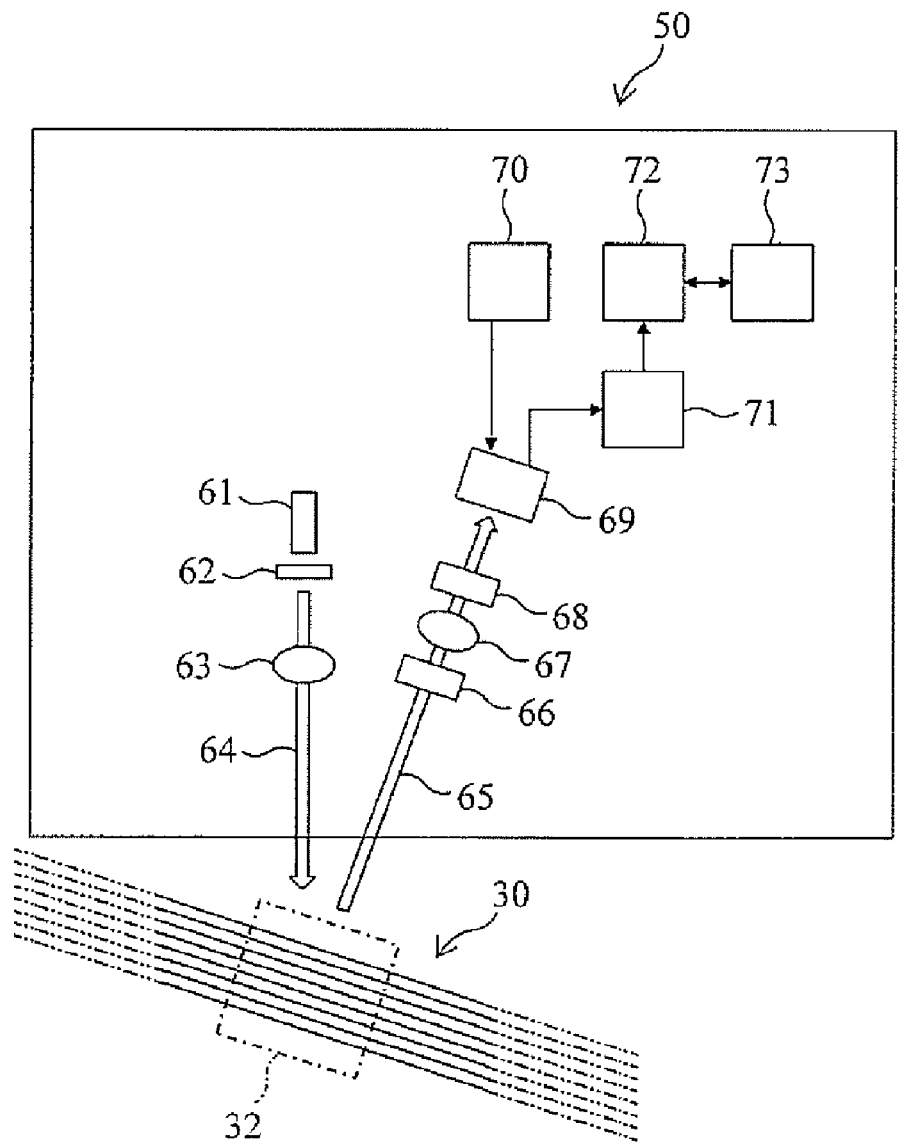

[Fig. 4]
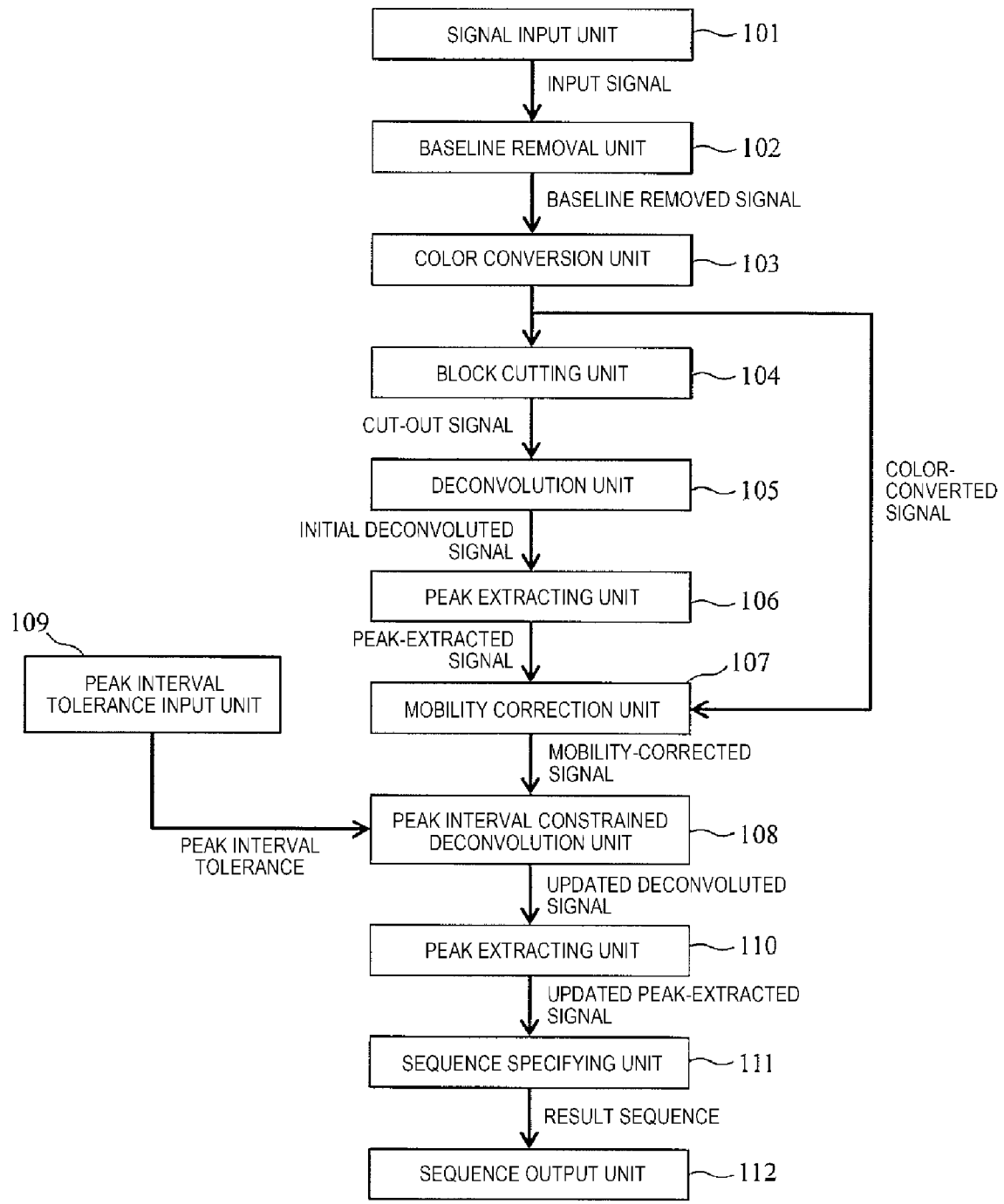

[Fig. 5]
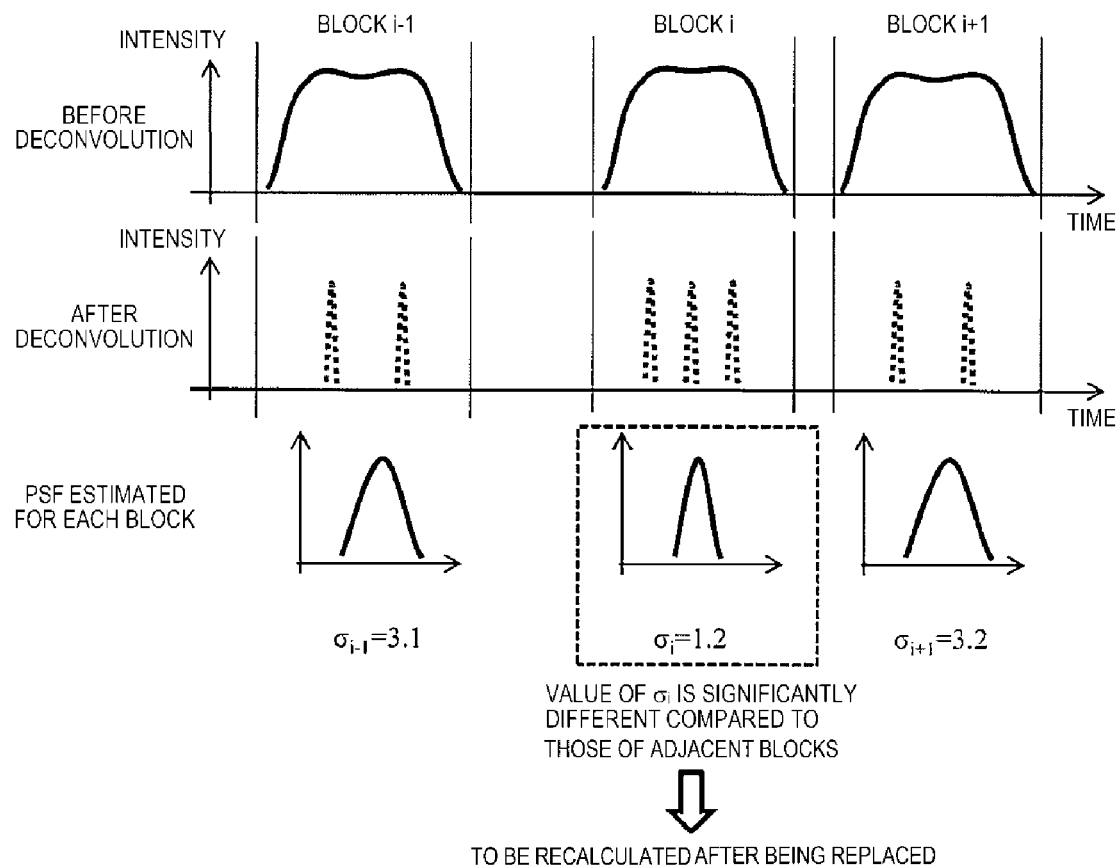

[Fig. 6]
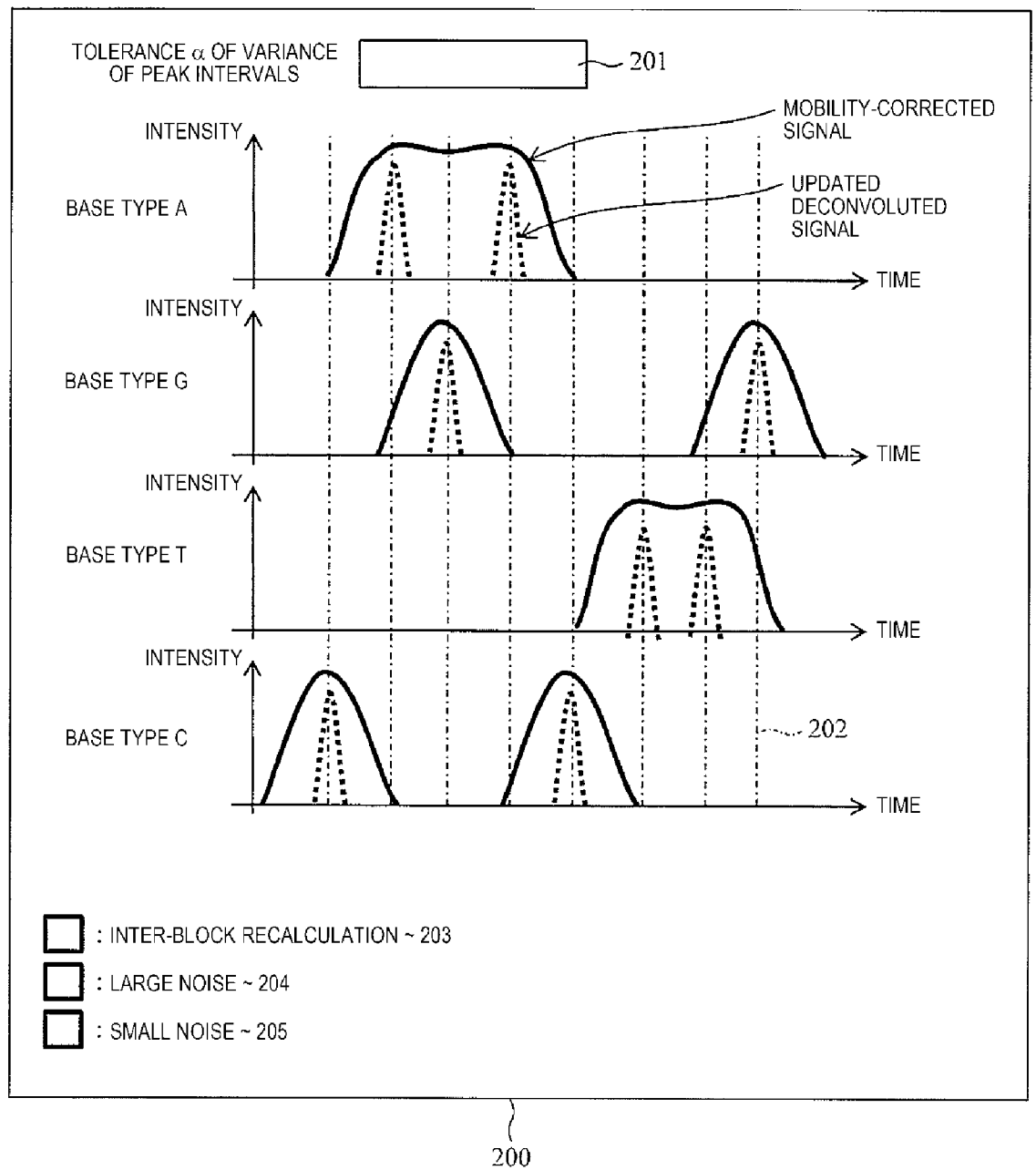

[Fig. 7]
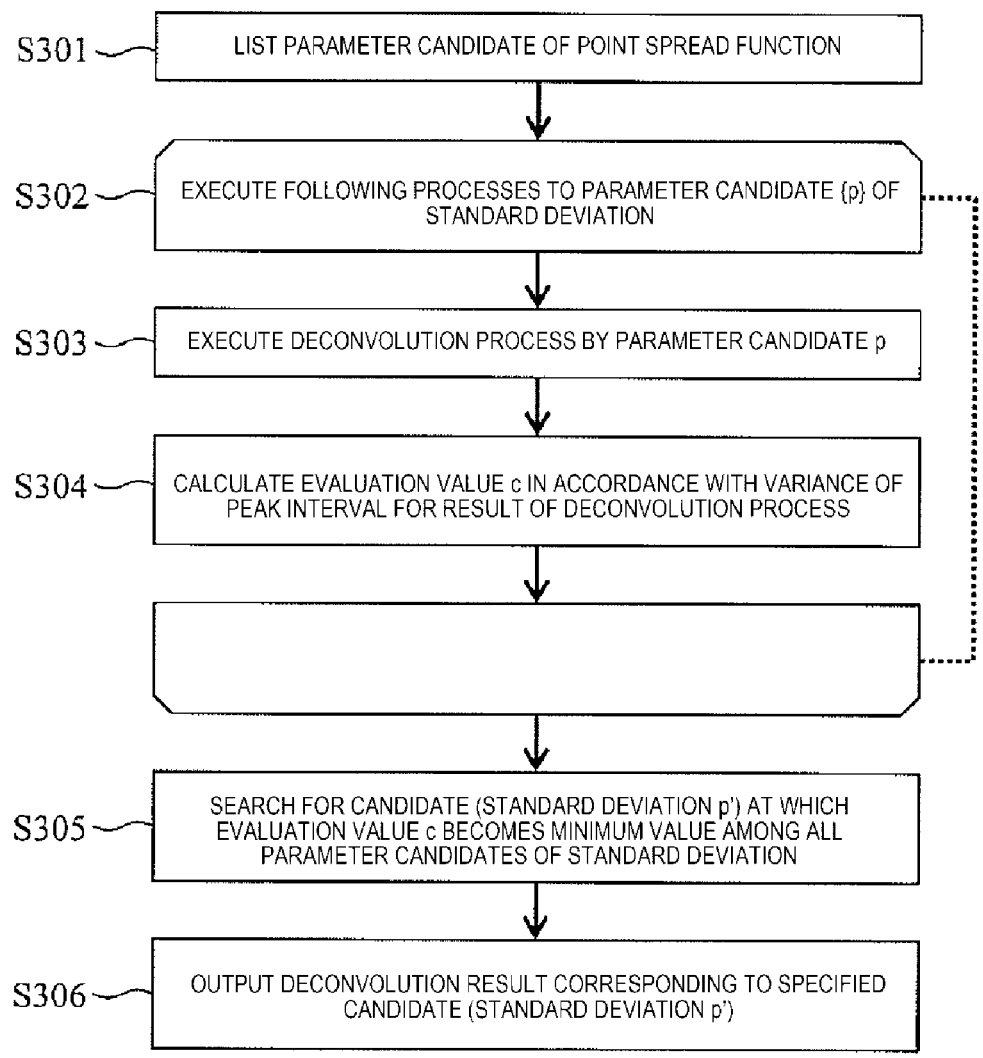

[Fig. 8]
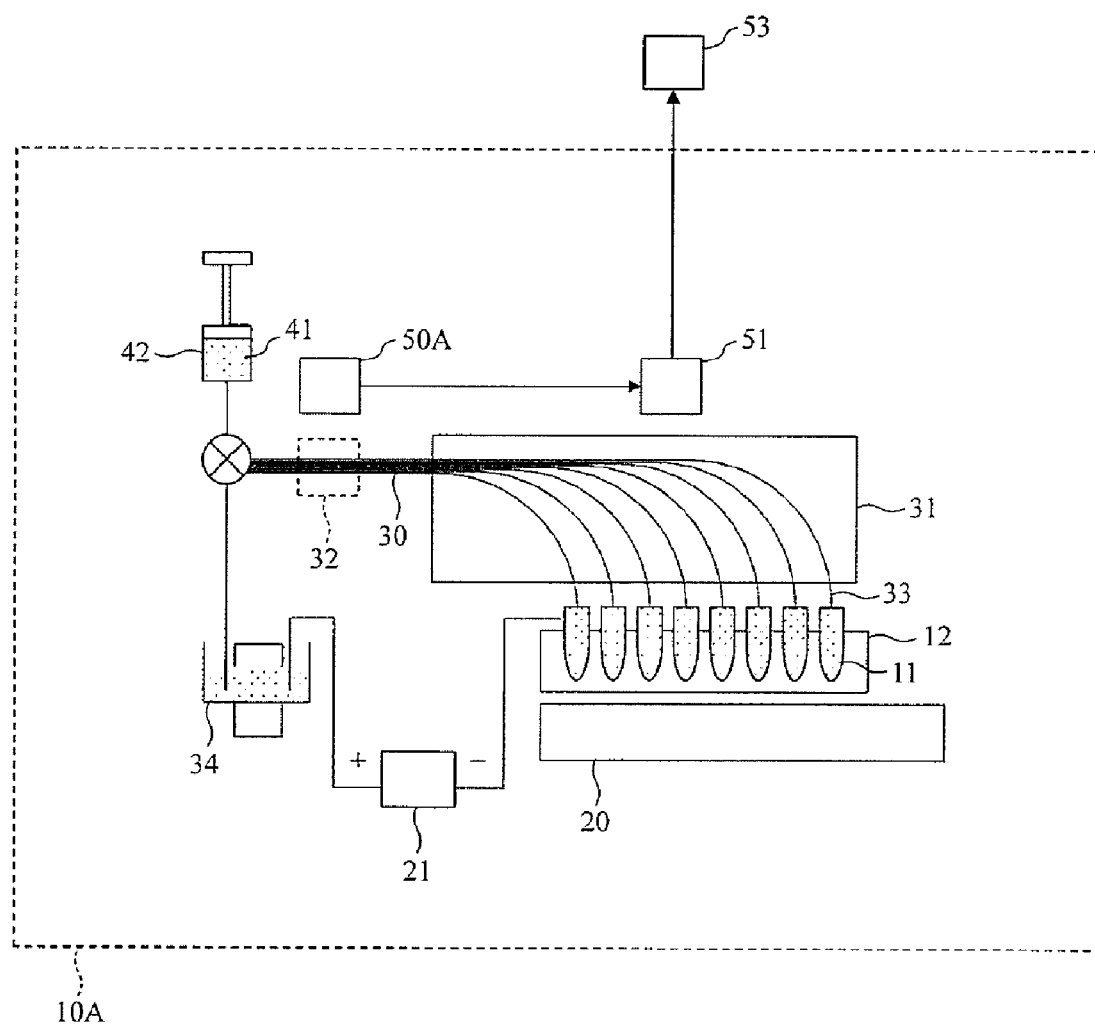

BASE SEQUENCE DETERMINATION APPARATUS, CAPILLARY ARRAY ELECTROPHORESIS APPARATUS, AND METHOD

TECHNICAL FIELD

The present invention relates to a technology for automatically determining a base sequence.

BACKGROUND ART

An apparatus for determining a base sequence constituting a nucleic acid is generally called a deoxyribonucleic acid (DNA) sequencer. Various types of detection technologies exist in the DNA sequencer. Hereinafter, a capillary electrophoresis sequencer will be described. The capillary electrophoresis sequencer determines a base sequence by electrophoresing a nucleic acid sample. The capillary electrophoresis sequencer observes wavelength spectra emitted from dyes corresponding to four kinds of bases (adenine (A), guanine (G), cytosine (C), thymine (T)) as a time series input signal and determines the base sequence. In this manner, a process of determining the base sequence from the time series input signal is called "base calling".

In the base calling, peaks corresponding to each base are detected from signals subjected to color conversion and mobility correction to an input signal, and a sequence is determined according to an order of positions of the peaks. However, steep peaks are not necessarily observed, and as the peaks overlap each other, the width of the peak may widen, and a plurality of overlapping peaks may be observed as one peak on the input signal. In this case, if one peak on the input signal is not decomposed into a plurality of original peaks and a correct position of each peak is not determined, the analysis becomes inaccurate.

There is a method described in PTL 1 as a method for determining a sequence with high accuracy even if there are such overlapping peaks. In Abstract of PTL 1, it is described that "(A) a basic peak extracting step in which basic peaks are extracted from electrophoretic data involving the respective peaks of the four bases obtained by electrophoresing a sample nucleic acid; (B) a condition determining step in which a basic peak at the search start point, from which the search is started, and a standard peak-to-peak distance are determined based on the time-series data composed of the basic peaks extracted above; and (C) a base sequence determining step wherein peak-to-peak intervals are successively scanned forward and backward in the above-described time-series data starting from the basic peak at the search start point and then the peak-to-peak distance is compared with the standard peak-to-peak distance as determined above so as to add an interpolation peak to a peak-missing area.".

CITATION LIST

Patent Literature

PTL 1: International Publication No. 2008/050426

SUMMARY OF INVENTION

Technical Problem

As described above, PTL 1 describes a technology of "comparing the interval between the basic peaks with the standard peak-to-peak distance and adding an interpolation peak to the peak missing area". However, in the method of adding the peak to the missing area, even if it is possible to determine the area to which the peak is added, it is not possible to determine which base type of peak should be added. For example, as illustrated in FIG. 1, a case where waveforms temporally overlap between base type A and base type G is considered. Although in a case where there is a minute peak P1 in the base type A, a peak P1 cannot be detected due to some cause such as noise, it is not clear whether the peak P1 is added to any one of base type A and base type G.

Therefore, the present invention provides a technology capable of determining the base sequence with high accuracy even in a case where a degree of separation of peaks is low.

Solution to Problem

In order to solve the above problem, the present invention employs, for example, the configuration described in the claims. The present specification includes a plurality of means for solving the above-described problem, one example of which includes a "base sequence determination apparatus including (1) a mobility correction unit that outputs a mobility correction signal obtained by mobility correction of a time-series signal of a wavelength spectrum corresponding to each base, (2) a deconvolution unit that executes a process of calculating a deconvoluted signal of the mobility correction signal respectively for a plurality of the parameter candidates of point spread function, a process of calculating variance of peak intervals for the calculated deconvoluted signal, a process of specifying a parameter of the point spread function using the calculated variance, and a process of outputting the deconvoluted signal corresponding to the point spread function having the specified parameter as an updated deconvoluted signal, (3) a peak extracting unit that extracts a peak waveform from the updated deconvoluted signal and outputs an updated peak-extracted signal, and (4) a sequence specifying unit that inputs the updated peak-extracted signal and determines abase sequence".

Advantageous Effects of Invention

According to the present invention, even in a case where the degree of separation of peaks is low, the base sequence can be determined with high accuracy. The problem, configuration, and effect other than those described above will be clarified by the following embodiments.

BRIEF DESCRIPTION OF DRAWINGS

FIG. 1 is a diagram illustrating a case where a degree of separation of peaks is low.

FIG. 2 is a diagram illustrating an overall configuration of a capillary electrophoresis apparatus according to Example 1.

FIG. 3 is a diagram illustrating a configuration of a fluorescence detection device according to Example 1.

FIG. 4 is a diagram illustrating a functional configuration of a signal processing unit.

FIG. 5 is a diagram illustrating a recalculation function (inter-block recalculation function) using standard deviations calculated for a plurality of blocks.

FIG. 6 is a diagram illustrating an example of a user interface screen.

FIG. 7 is a flowchart illustrating a processing operation of a peak interval constrained deconvolution unit.

FIG. 8 is a diagram illustrating another configuration example of a capillary electrophoresis apparatus.

DESCRIPTION OF EMBODIMENTS

Hereinafter, embodiments of the present invention will be described below with reference to the drawings. The embodiments of the present invention are not limited to the embodiments described later, and various modifications are possible within the scope of the technical idea thereof.

(1) EXAMPLE 1

(1-1) Overall Configuration

FIG. 2 illustrates a configuration example of a capillary array electrophoresis apparatus 10. The capillary array electrophoresis apparatus 10 includes a sample tray 12 that accommodates a plurality of the sample containers 11 (each sample container 11 contains different sample) containing a sample to which a fluorescent label is attached to DNA as a measurement object (hereinafter, referred to as a "sample"), a transporter 20 that transports the sample tray 12, a capillary array 30 serving as an electrophoresis path of the sample in the sample container 11, a pump unit 42 that injects an electrophoretic medium 41 into the capillary array 30, a high voltage power supply 21 that applies a high voltage to both ends of the capillary array 30, a constant temperature reservoir 31 that keeps an interior of the capillary array 30 at a constant temperature, a detection position 32 provided on a path for electrophoresis of the sample, a fluorescence detection device 50, and a control substrate 51.

The capillary array 30 is an aggregate of a plurality of capillaries 33. Each of the capillaries 33 is hollow. In a case of this example, a length of the capillary 33 is 30 cm or less. However, the length of the capillary 33 may be 30 cm or more (for example, 36 cm or more). In addition, one end of each of the capillaries 33 is inserted into a sample in the sample container 11. The sample moves from the sample container 11 into the capillary 33. Thereafter, the sample electrophoreses inside the capillary. The pump unit 42 injects the electrophoretic medium 41 (for example, a polymer) into each of the capillaries 33. Accordingly, the interior of each of the capillaries 33 is filled with the electrophoretic medium 41.

The high voltage power supply 21 applies a high voltage (for example, the maximum voltage of 20 kV) to both ends of each of the capillaries 33 filled with the electrophoretic medium 41. By application of the high voltage, each sample passes through each of the capillaries 33 and electrophoreses from the sample container 11 to the detection position 32. Each of samples which have passed through the detection position 32 electrophoreses toward a discharge position 34. Since a migration speed of the sample varies depending on its base length, the sample arrives at the detection position 32 in order from the DNA with short base length.

The fluorescence detection device 50 sequentially radiates excitation light from the sample arriving at the detection position 32 and detects a fluorescence signal intensity and wavelength emitted from a fluorescent label. The fluorescence detection device 50 in the present example determines the base sequence of DNA based on the wavelength of the detected fluorescence signal and outputs the determined base sequence to the control substrate 51. In addition, the fluorescence detection device 50 displays information other than the determined base sequence on a screen of a display device 52. The control substrate 51 transfers the base sequence of the fluorescence signal analyzed by the fluorescence detection device 50 to an external terminal (not illustrated). It is desirable that the external terminal here has a display device for confirming the analysis result.

FIG. 3 illustrates an internal configuration example of the fluorescence detection device 50. The fluorescence detection device 50 includes an excitation light source 61, a shutter 62, an excitation light lens 63, an optical filter 66, a fluorescent lens 67, a diffraction grating 68, a charge coupled device (CCD) 69, a CCD control unit 70, an analog to digital converter (ADC) 71, a signal processing unit 72, and a memory 73.

The excitation light source 61 is a light source that continuously emits an excitation light 64. All the capillaries 33 corresponding to the detection position 32 are irradiated with the excitation light 64. The shutter 62 repeatedly opens and closes at predetermined intervals. The shutter 62 transmits the excitation light 64 irradiated from the excitation light source 61 at the time of opening, and shuts off at the time of closing. The excitation light lens 63 condenses the excitation light 64 transmitted through the shutter 62. The excitation light 64 condensed by the excitation light lens 63 is radiated toward the detection position 32. By electrophoresis, the fluorescent label added to the DNA passing through the detection position 32 of each of the capillaries 33 is excited by irradiation with the excitation light 64, and emits a fluorescence signal 65.

The optical filter 66 (for example, a color filter) cuts light other than the fluorescence signal 65 emitted from the fluorescent label. The fluorescent lens 67 condenses the fluorescence signal 65 passing through the optical filter 66. The fluorescence signal 65 collected by the fluorescent lens is spectrally separated for each wavelength by the diffraction grating 68 and is radiated to the light receiving surface of the CCD 69 that is a light receiving element (light receiving unit). When the fluorescence signal 65 dispersed for each wavelength is radiated, signal charges are generated on the light receiving surface of the CCD 69. A conversion circuit of the CCD 69 converts the signal charge to a voltage (analog) and outputs the voltage to the ADC 71. The CCD 69 may be any of a frame transfer CCD, a full frame transfer CCD, an interline transfer CCD, and a frame inter transfer CCD.

The ADC 71 converts the analog signal output from the CCD 69 into a digital signal. The ADC 71 outputs the converted digital signal to the signal processing unit 72. The signal processing unit 72 acquires the fluorescence signal intensity (corresponding to the fluorescence signal intensity of the light receiving surface that is pseudo-combined as one pixel) from the output digital signal. The signal processing unit of the present example executes a signal process for determining the base sequence of DNA based on the wavelength of the fluorescence signal obtained from the digital signal. The signal processing unit 72 stores the fluorescence signal intensity and wavelength obtained from the output digital signal in the memory 73.

(1-2) Functional Configuration of Signal Processing Unit 72

FIG. 4 illustrates a functional configuration of the signal processing unit 72. In the case of the present example, the function of the signal processing unit 72 is realized through execution of a program by a computer. A signal input unit 101 receives an input signal which is a digital signal from the ADC 71. As described above, the input signal is a time series of wavelength spectra emitted from dyes corresponding to each of the four kinds of bases of each base type adenine (A), guanine (G), cytosine (C), thymine (T).

The wavelength spectrum at each time is an array of real numbers discretizing each wavelength, and an array length N thereof is an integer of 4 or more, such as 10 or 20. Therefore, the input signal is an N-channel real valued signal.

A baseline removal unit 102 executes a baseline removal process to obtain a baseline-removed signal from the input signal (N-channel real valued signal). In the baseline removal process, a known method such as subtracting the minimum value of the neighborhood interval at each time may be used. A color conversion unit 103 executes a color conversion process and calculates a color-converted signal, which is a 4-channel signal corresponding to each of the four types of bases, from the baseline-removed signal (N-channel real valued signal). For the color conversion process, a known method such as multiplication of a pseudo inverse matrix of a preliminarily calibrated color conversion matrix may be used.

A block cutout unit 104 executes a block cutout process for dividing the signals of each channel of the color-converted signal into small sections (hereinafter, also referred to as "blocks"), with the time at which the intensity is sufficiently small, and outputs the signals corresponding to each block as a cut-out signal. FIG. 5 illustrates an example of cutting out the block. As illustrated in FIG. 5, one cut-out signal is configured of a single wave shape. By dividing the signals into blocks, it is possible to reduce an amount of calculations such as a deconvolution process of a subsequent stage or a deconvolution process with peak interval constraint. Accordingly, it is possible to shorten the processing time and reduce memory consumption.

A deconvolution unit 105 performs deconvolution processing on the cut-out signal to calculate an initial deconvoluted signal. In general, the deconvolution process is different in difficulty between a case where a point spread function (PSF) is known and in a case where the PSF is unknown. In a case where the PSF is known, the deconvolution process is a process of calculating a deconvoluted signal using an input signal (cut-out signal) and the PSF. In this case, it is possible to perform deconvolution with relatively high accuracy by a method using a Wiener filter or the like.

Meanwhile, in the capillary electrophoresis apparatus 10, the PSF may vary in some cases. Accordingly, the deconvolution unit 105 is required to perform deconvolution under a condition where the PSF is unknown. This process is a process of calculating both the PSF and the deconvoluted signal using the input signal, and is called "blind deconvolution". For example, deconvolution with such simultaneous optimization is feasible based on nonnegative matrix factorization (NMF). However, in general, there are countless candidates for the set of the PSF and the deconvoluted signal, and countless local solutions thereof exist. Therefore, it is generally difficult to obtain a highly accurate solution. In the NMF, there is a strategy to obtain a global solution by avoiding local solutions such as sparse regularization such as L1 regularization and L1/L2 regularization. However, it is difficult to obtain sufficient accuracy even when the strategy is used in the capillary electrophoresis apparatus 10.

Therefore, in the deconvolution unit 105 of this example, candidate solutions are reduced by the method described below, and local solutions are avoided. First, the deconvolution unit 105 limits the PSF to a Gaussian function and limits the unknown parameter to only the standard deviation $\sigma$. In this way, the local solutions can be avoided by limiting unknown parameters of the PSF. The deconvolution unit 105 performs a deconvolution process on the discretized finite number of standard deviations $\sigma$ using the corresponding Gaussian function as a PSF to obtain deconvoluted signals for each of the standard deviations $\sigma$.

Next, the deconvolution unit 105 narrows the solution candidates to only the set of the standard deviation $\sigma$ and the deconvoluted signal that satisfy the following conditions (1), (2) and (3).

(1) $e(\sigma)$ calculated below is less than or equal to a certain threshold.

First, the deconvolution unit 105 executes a convolution process using the Gaussian function corresponding to the standard deviation $\sigma$ and a deconvoluted signal using the Gaussian function, and calculates the convoluted signal. Next, the deconvolution unit 105 calculates an error $e(\sigma)$ between the convoluted signal and the input signal for each standard deviation $\sigma$ based on a mean square error or Kullback-Leibler divergence. Next, only the standard deviation $\sigma$ where the error $e(\sigma)$ is equal to or less than a certain threshold value is selected. With this condition, only solutions according to a convolution generation model can be narrowed down to parameter candidates.

(2) For each interval of peaks extracted from the deconvoluted signal, the minimum value of the peak interval in the block is equal to or more than a certain threshold value.

With this condition, the local solutions can be avoided by excluding candidates of solutions where peak intervals are too short.

(3) $\sigma$ is near an inflection point $\sigma\_r$ of $e(\sigma)$.

For example, the deconvolution unit 105 detects a positive peak of a secondary differential value $e''(\sigma)$ relating to $\sigma$ of the error $e(\sigma)$ as the inflection point, and substitutes the position of the peak into the inflection point $\sigma\_r$. With this condition, it is possible to exclude such a solution that the number of peaks is excessive than originally. This is due to the following reasons. $e(\sigma)$ corresponding to the solution in which the number of peaks is excessive than originally is a value that is as small as $e(\sigma)$ corresponding to the original solution. In addition, $e(\sigma)$ corresponding to the solution where the number of peaks is smaller than the originally is a value larger than $e(\sigma)$ corresponding to the original solution. Therefore, it can be considered that $\sigma$ at which $e(\sigma)$ steeply changes, that is, the solution corresponding to the inflection point $\sigma\_r$ is close to the original solution.

By executing the above processes, the deconvolution unit 105 calculates the standard deviation $\sigma$ and the deconvoluted signal for each block. Here, as illustrated in FIG. 5, the standard deviation of the i-th block is defined as $\sigma\_i$. It can be assumed that the standard deviation $\sigma$ does not vary greatly in a short time. Under this assumption, the deconvolution unit 105 also has a function (inter-block recalculation function) for further improving the accuracy of deconvolution.

When executing this function, the deconvolution unit 105 determines whether or not the difference between the standard deviation $\sigma$ of the block and the average value of the standard deviations of blocks appearing before and after the block exceeds a threshold value T.

$$|\sigma_i - \text{median}\{\sigma_j\}_{j=i-K}^{j=i+K}| > T \quad \text{Expression 1}$$

In a case where Expression 1 is established, the deconvolution unit 105 performs deconvolution again with the PSF with the value given by Expression 2 as the standard deviation, and calculates a new deconvoluted signal. Where, K is a constant of a certain natural number (1, 2, 3, . . . ).

$$\mathrm{median}\{\sigma_j\}_{j=i-K}^{j=i+K} \qquad \text{Expression 2}$$

For example, in the case of FIG. 5, since the standard deviation $\sigma_i$ of the i-th block is "1.2", which is greatly different from the average value "3.15" of the standard deviations of the previous or next blocks, the deconvolution unit 105 recalculates the deconvoluted signal of the i-th block. The recalculation function taking account of the plurality of blocks may be automatically performed by the deconvolution unit 105. As described later, an operator may designate the execution or non-execution of the function on a user interface screen. The screen illustrated in FIG. 5 may be presented to the operator as an interface screen.

Returning to the description of FIG. 4. A peak extracting unit 106 executes a peak extracting process and obtains a peak-extracted signal from the initial deconvoluted signal. For the peak extracting process, a known method such as a calculation method for calculating a zero crossing of a first derivative may be used.

The mobility correction unit 107 executes a mobility correction process and calculates a mobility-corrected signal from the peak-extracted signal and the color-converted signal. The mobility correction process is executed in the following procedure.

(1) The mobility correction unit 107 substitutes the peak-extracted signal into a "mobility correction in-progress peak signal" and substitutes the post-color conversion signal into the "mobility correction in-progress signal".

(2) For a peak PG corresponding to a base other than guanine (G) adjacent to the rear of the peak PG of guanine (G) on the time axis among the peaks PG of guanine (G), the mobility correction unit 107 calculates an average interval d(G) between a peak PG and a peak of another base adjacent to the peak PG on the time axis behind the peak to the mobility correction in-progress peak signal. Similarly, for a peak PA corresponding to a base other than adenine (A) adjacent to the rear of the peak PA of adenine (A) on the time axis among the peaks PA of adenine (A), the mobility correction unit 107 calculates an average interval d(A) between a peak PA and a peak of another base adjacent to the peak PA on the time axis behind the peak. Similarly, for a peak PT corresponding to a base other than thymine (T) adjacent to the rear of the peak PT of thymine (T) on the time axis among the peaks PT of thymine (T), the mobility correction unit 107 calculates an average interval d(T) between a peak PT and a peak of another base adjacent to the peak PT on the time axis behind the peak. Similarly, for a peak PC corresponding to a base other than cytosine (C) adjacent to the rear of the peak PC of cytosine (C) on the time axis among the peaks PC of cytosine (C), the mobility correction unit 107 calculates an average interval d (C) between a peak PC and a peak of another base adjacent to the peak PC on the time axis behind the peak.

(3) The mobility correction unit 107 calculates an average value d_mean of d(G), d(A), d(T), and d(C).

(4) The mobility correction unit 107 calculates d'(G), d'(A), d'(T), and d'(C) given by the following equations.

$$d'(G)=d(G)-d\_\mathrm{mean}$$

$$d'(A)=d(A)-d\_\mathrm{mean}$$

$$d'(T)=d(T)-d\_\mathrm{mean}$$

$$d'(C)=d(C)-d\_\mathrm{mean}$$

(5) The mobility correction unit 107 shifts a channel corresponding to guanine (G) of the mobility correction in-progress peak signal rearward by d'(G) on the time axis, shifts a channel corresponding to adenine (A) rearward by d'(A) on the time axis, shifts a channel corresponding to thymine (T) rearward by d'(T) on the time axis, shifts a channel corresponding to cytosine (C) rearward by d'(C) on the time axis, and overwrites the mobility correction in-progress peak signal with the shifted signal.

(6) The mobility correction unit 107 shifts a channel corresponding to guanine (G) of the mobility correction in-progress signal rearward by d'(G) on the time axis, shifts a channel corresponding to adenine (A) rearward by d'(A) on the time axis, shifts a channel corresponding to thymine (T) rearward by d'(T) on the time axis, shifts a channel corresponding to cytosine (C) rearward by d'(C) on the time axis, and overwrites the mobility correction in-progress signal with the shifted signal.

(7) In a case where any of d'(G), d'(A), d'(T), and d'(C) is sufficiently small (smaller than each threshold value), the mobility correction unit 107 substitutes the overwritten mobility correction in-progress signal into the mobility-corrected signal and ends the process. Otherwise, the process returns to the process (2).

A peak interval tolerance input unit 109 executes a process of receiving an input of the tolerance $\alpha$ of the variance of the peak interval by the operator through the interface screen displayed on the screen of the display device 52. $\alpha$ means a tolerance as to how much the variance of the peak interval is permitted. Since the operator can set $\alpha$ through the peak interval tolerance input unit 109, the base calling can be performed with high accuracy using the optimum $\alpha$ depending on the noise magnitude.

FIG. 6 illustrates an example of an interface screen 200 displayed by the peak interval tolerance input unit 109. Waveforms of the mobility-corrected signal and the updated deconvoluted signal obtained by processing time series of each wavelength spectrum emitted from dyes corresponding to bases adenine (A), guanine (G), cytosine (C), thymine (T) are displayed on the interface screen 200 illustrated in FIG. 6.

An entry field 201 of the tolerance $\alpha$ of the variance of the peak interval is provided on the interface screen 200. An updated deconvoluted signal calculated using the input tolerance $\alpha$ is displayed on the interface screen 200. Accordingly, when the value of the tolerance $\alpha$ is changed, the waveform of the displayed updated deconvoluted signal also changes. By confirming the updated deconvoluted signal calculated using the tolerance $\alpha$, the operator can easily determine whether the input tolerance $\alpha$ is an appropriate value or not.

In addition, the peak interval tolerance input unit 109 also displays the peak positions 202 extracted based on the updated deconvoluted signal calculated using the input tolerance $\alpha$. In FIG. 6, the peak positions 202 are indicated by a one-dot chain line. By confirming whether or not the interval between the peak positions 202 is constant, the operator can easily determine whether the input tolerance $\alpha$ is an appropriate value or not. As the interval of the peak positions 202 is closer to constant, the input tolerance $\alpha$ is close to the appropriate value. In addition, by comparing the mobility-corrected signal with the updated deconvoluted signal which are displayed on the interface screen 200, the operator can easily determine whether the deconvolution process is properly executed or not. That is, it can be easily determined whether the tolerance α is an appropriate value or not. A check column 203 for selecting a presence or absence of execution of the inter-block recalculation function of the deconvolution unit 105, a check column 204 for instructing the execution of calculation process in the case of a large noise, and a check column 205 for instructing the execution of the calculation process in the case of a small noise are also provided on the interface screen 200. The process content in the case where the check column 203 is checked has already been described with reference to FIG. 5. The process contents in a case where the check column 204 or 205 are checked will be described later. FIG. 6 is an example of the interface screen 200, and the entry field 201 and the check columns 203 to 205 may not be displayed, or only a part thereof may be displayed.

Returning to the description of FIG. 4. A peak interval constrained deconvolution processing unit 108 performs a deconvolution process on the 4-channel mobility-corrected signal to calculate the 4-channel updated deconvoluted signal. As described above, in a case where the PSF is unknown, it is difficult to obtain sufficient accuracy by deconvolution process. Therefore, a peak interval constrained deconvolution processing unit 108 of the present example avoids local solutions by reducing solution candidates as follows.

FIG. 7 illustrates the processing operation of the peak interval constrained deconvolution processing unit 108. First, the peak interval constrained deconvolution processing unit 108 limits the PSF to a Gaussian function and limits the unknown parameter to only the standard deviation σ. In this way, the local solutions can be avoided by limiting unknown parameters of the PSF. Next, the peak interval constrained deconvolution processing unit 108 lists the discretized finite number of standard deviations σ as parameter candidates (step S301), and executes the following processing for each parameter candidate (step S302). First, the peak interval constrained deconvolution processing unit 108 performs a deconvolution process using the Gauss function corresponding to the standard deviation of the processing target as the PSF to obtain a 4-channel deconvoluted signal (step S303).

Next, the peak interval constrained deconvolution processing unit 108 calculates e(σ) and v(σ) in the procedure of (1) and (2) below for the parameter candidate to be processed (that is, the standard deviation σ).

(1) Similar to the above-described processes, the peak interval constrained deconvolution processing unit 108 executes a convolution process using the Gaussian function corresponding to the standard deviation σ and a deconvoluted signal using the Gaussian function, and calculates the 4-channel convoluted signal. Next, the peak interval constrained deconvolution processing unit 108 calculates the error e(σ) between the calculated convoluted signal and the input signal based on a mean square error or Kullback-Leibler divergence.

(2) For each peak extracted from the calculated 4-channel convoluted signal, the peak interval constrained deconvolution processing unit 108 calculates the interval between adjacent peaks specified by ignoring the channel difference. Details have already been described with reference to FIG. 6. Next, the peak interval constrained deconvolution processing unit 108 calculates a variance value v(σ) for all the peaks corresponding to these intervals. However, v(σ) is not a literal variance value, it may be the maximum value of the deviation from the standard deviation or average value or a median absolute deviation (MAD). In this specification, the term "variance" is used in a generic sense.

Next, the peak interval constrained deconvolution processing unit 108 calculates the evaluation value c by the following expression (step S304).

$$c = e(\sigma) + \alpha \times v(\sigma) \quad \text{Expression 3}$$

α is the tolerance of variance of the peak interval, as described above. For example, in a case where the noise is large, the peak interval constrained deconvolution processing unit 108 emphasizes the variance v(σ) of the peak interval by setting the tolerance α to be large. Accordingly, even when the convolution error e(σ) is large, an allowable solution is obtained. On the other hand, in a case where the noise is small, the peak interval constrained deconvolution processing unit 108 emphasizes the convolution error e(σ) by setting the tolerance α to be small, and even when the variance v(σ) of the peak interval is large, the acceptable solution is obtained.

Incidentally, the determination as to whether the noise is large or not may be automatically executed by the peak interval constrained deconvolution processing unit 108. In addition, as illustrated in FIG. 6, a mechanism that the peak interval constrained deconvolution processing unit 108 detects that the operator checks one of the check columns 204 and 205 on the interface screen 200 to change the magnitude of the tolerance α in accordance with the check contents may be adopted.

The peak interval constrained deconvolution processing unit 108 searches for a standard deviation at which the evaluation value c become a minimum value (step S305), and outputs the 4-channel convoluted signal corresponding to the specified standard deviation with as the 4-channel updated deconvoluted signal (step S306). The updated deconvoluted signal obtained in this manner satisfies the constraint that the peak interval is substantially constant. Since there is a high possibility that the original solution such solutions, it is a deconvolution result with sufficient accuracy. Depending on the calculation formula used to calculate the evaluation value c, the standard deviation adopting the maximum value may be searched.

The above processes are executed for each of the blocks (see FIG. 5). Similar to the above-described deconvolution unit 105, the process of the peak interval constrained deconvolution processing unit 108 can further improve the accuracy by using the results calculated for a plurality of blocks. In also here, the standard deviation σ of the i-th block is defined as σ_i. In also here, it is assumed that the standard deviation σ does not vary greatly in a short time. The peak interval constrained deconvolution processing unit 108 determines whether or not the difference between the standard deviation σ of the block and the average value of the standard deviations of blocks appearing before and after the block exceeds a threshold value T.

$$\left| \sigma_i - \text{median}\{\sigma_j\}_{j=i-K}^{j=i+K} \right| > T \quad \text{Expression 4}$$

In a case where Expression 4 is established, the peak interval constrained deconvolution processing unit 108 performs deconvolution again with the PSF with the value given by Expression 5 as the standard deviation, and calculates a new deconvoluted signal. Where, K is a constant of a certain natural number (1, 2, 3, . . . ).

$$\text{median}\{\sigma_j\}_{j=i-K}^{j=i+K} \quad \text{Expression 5}$$

Returning to the description of FIG. 4. A peak extracting unit 110 executes a process of extracting the peak waveform and calculates the 4-channel updated peak-extracted signal from the 4-channel updated deconvoluted signal. For the peak extracting process, a known method of calculating the zero crossing of the first derivative of the updated deconvoluted signal and replacing the signal value of the updated peak-extracted signal at the time when the zero crossing exists by the signal value of the updated deconvoluted signal may be used. For the calculation of the first derivative of the updated deconvoluted signal, spline interpolation is performed on the updated deconvoluted signal, and the first derivative value of the signal after the spline interpolation is calculated. Therefore, it is possible to extract peaks robust against noise.

For the purpose of further improving the accuracy, the peak extracting unit 110 may execute a determination process based on the following determination rule for all peaks and delete the peak determined to be "deleted" as a result of the determination.

Determination rule: Delete if d<0 is satisfied. Where, d is a discriminant function depending on x_1 and x_2 below.

x_1=Intensity of target peak−Average value of intensity of adjacent peaks x_2=Intensity of channel of target peak at time of target peak in mobility-corrected signal/average intensity over channel at time of target peak in mobility-corrected signal For example, in d, a linear discrimination function d=w_1*x_1+w_2*x_2+w_3 may be used, a support vector machine (SVM) may be used, or a decision tree may be used.

A sequence specifying unit 111 executes a sequence specifying process and outputs the result sequence from the 4-channel updated peak-extracted signal. In the sequence specifying process, labels G, A, T, and C of base types corresponding to respective peaks in the updated peak-extracted signal are arranged in chronological order to generate a label sequence. This label sequence is defined as the result sequence. A sequence output unit 112 outputs the result sequence to a storage device such as a hard disk or a solid state drive (SSD), or presents the result sequence using the display device 52.

(1-3) Summary

As described above, the capillary array electrophoresis apparatus 10 of the present example is equipped with the function of executing the deconvolution process after restricting the peak interval. Accordingly, even in a case where the degree of separation of peaks is low (specifically, a case where waveforms of different base types temporally overlap), the base sequence can be determined with high accuracy. In particular, in portable (compact) sequencers and sequencers with short measuring time, since it is considered that the degree of separation of peaks is likely to be low, the method of the present example is effective for these sequencers.

(2) EXAMPLE 2

In the present example, a case where the capillary array electrophoresis apparatus 10 employs a function of machine learning of various parameters will be described. The basic apparatus of the capillary array electrophoresis apparatus in the present example is the same as in Example 1. Hereinafter, it is assumed that a plurality of input signals obtained by measuring samples of known base sequences under the same measurement conditions are input to the signal input unit 101.

First, as a learning process 1, a method of automatically tuning the tolerance α of variance of peak intervals will be described. The signal processing unit 72 changes the tolerance α with a certain increment Δα within a certain range [α_min and α_max], executes a series of processing described in Example 1 using each α, and determine the base sequence. Thereafter, the signal processing unit 72 calculates a coincidence rate p(α) between the base sequence determined using each tolerance α and the correct sequence, and calculates the tolerance α so that the coincidence rate p(α) becomes a maximum value is set. By executing this learning process, it is possible to omit the input of the tolerance α using the user interface screen 200.

Next, as a learning process 2, a method of tuning parameters other than the tolerance α will be described. The signal processing unit 72 performs turning of the parameters w_1, w_2, and w_3 of the deletion determination rule of the peak extracting unit 110 described in Example 1, for example. Here, since the sample whose base sequence is known is measured, it is possible to determine whether the originally existing peak is correctly extracted, a peak which does not originally exist is erroneously extracted, the originally existing peak is not excluded by erroneously extraction, or a peak which does not originally exist is excluded correctly, for each peak. The correctness is regarded as a teacher signal, and the signal processing unit 72 performs supervised learning with the output signal d.

In a case where the output signal d is a linear discrimination function, the signal processing unit 72 may use an algorithm such as error correction learning. In a case where the output signal d is a support vector machine (SVM), the signal processing unit 72 can use a sequential minimal optimization (SMO) algorithm for supervised learning. In a case where the output signal d is a decision tree, the signal processing unit 72 can perform supervised learning with an algorithm such as ID3 or C4.5.

The result of learning process 1 and the result of learning process 2 have a dependence relationship with each other. Therefore, the signal processing unit 72 alternately performs the learning process 1 and the learning process 2, thereby executing the optimum parameter tuning as a whole.

(3) EXAMPLE 3

FIG. 8 illustrates another configuration example of a capillary array electrophoresis apparatus 10A. In FIG. 8, parts corresponding to those in FIG. 2 are denoted by the same reference numerals. In the case of Example 1 determination process of the base sequence is executed by the signal processing unit 72 of the fluorescence detection device 50. However, in a fluorescence detection device 50A of the present example, the base sequence analysis function is not mounted on the signal processing unit 72. It is executed by an external device 53 such as a computer externally attached to the capillary array electrophoresis apparatus 10A. For this reason, in the capillary array electrophoresis apparatus 10A illustrated in FIG. 8, the external device 53 is connected to the control substrate 51. It is assumed that the external device 53 has sufficient computational resources to execute the signal process executed by the signal processing unit 72. In addition, the external device 53 is provided with a display device for confirming process results and the like. The communication between the control substrate 51 and the external device 53 may be wired or wireless communication. For example, the external device 53 is a desktop PC, a notebook PC, a smartphone, or a portable information terminal.

(4) OTHER EXAMPLES

The present invention is not limited to the above-described example, and various modifications are included. For example, the above-described example has been described in detail so that the present invention is easily understood, and not limited to the one necessarily including all configurations described. A part of the configuration of an example can be replaced with the configuration of other examples, and the configuration of other examples can be added to the configuration of an example. In addition, other configurations can be added to, deleted from, or replaced with the part of the configuration of each example.

In addition, a part or all of each configuration, function, processing part, processing means, or the like described above may be realized by hardware, for example, by designing an integrated circuit. In addition, each configuration, function, or the like described above may be realized by software in which a processor interprets and executes a program that realizes each function.

Information on the program, a table, a file, or the like which realize each function can be placed in a recording device such as a memory, a hard disk, or an SSD, or in a recording medium such as an IC card, an SD card, or a DVD.

In addition, a control line or an information line considered to be necessary for explanation is indicated, and all the control lines or the information lines in the product are not necessarily indicated. Actually, it could be considered that almost all configurations are mutually connected.

REFERENCE SIGNS LIST

10: capillary array electrophoresis apparatus
11: sample container
12: sample tray
20: transporter
21: high voltage power supply
30: capillary array
31: constant temperature reservoir
32: detection position
33: capillary
34: discharge position
41: electrophoretic medium
42: pump unit
50: fluorescence detection device
51: control substrate
52: display device
72: signal processing unit
101: signal input unit
102: baseline removal unit
103: color conversion unit
104: block cutting unit
105: deconvolution unit
106: peak extracting unit
107: mobility correction unit
108: peak interval constrained deconvolution unit
109: peak interval tolerance input unit
110: peak extracting unit
111: sequence specifying unit
112: sequence output unit
200: interface screen
201: entry field of tolerance α
202: peak position
203: check column
204: check column
205: check column

The invention claimed is:
1. A base sequence determination apparatus comprising:
a memory;
an input device;
a sequence output device; and
a processor communicatively coupled to the memory, the input device and the sequence output device, wherein the processor is configured to:
divide a plurality of signals of each channel of a color-converted signal into multiple blocks;
output a mobility correction signal obtained by mobility correction of a time-series signal of a wavelength spectrum corresponding to each base using the multiple blocks;
receive, via the input device, a tolerance that gives a weighting coefficient;
changes the tolerance with an increment to a changed tolerance, the increment being within a range;
execute a process of calculating a deconvoluted signal of the mobility correction signal respectively for a plurality of parameter candidates of point spread function, a process of calculating variance of peak intervals for the calculated deconvoluted signal, a process of specifying a parameter of the point spread function using the calculated variance and the changed tolerance, and a process of outputting the deconvoluted signal corresponding to the point spread function having the specified parameter as an updated deconvoluted signal;
a peak waveform from the updated deconvoluted signal and outputs an updated peak-extracted signal;
receive the updated peak-extracted signal and determine a base sequence;
calculate a coincidence rate between the base sequence and a correct sequence; and
calculate, using machine learning, an updated tolerance causing the coincidence rate to be set at a maximum value, such that the updated deconvolution signal is calculated using the updated tolerance; and
tune, using machine learning, a plurality of parameters to determine a level of accuracy of the original peak, and
wherein calculating the updated tolerance and tuning the plurality of parameters are alternately performed such that the specified parameter is optimized each time.

2. The base sequence determination apparatus according to claim 1,
wherein the processor calculates a convolution error and the variance of the peak interval for the deconvoluted signal calculated for the plurality of parameter candidates, and specifies a parameter of the point spread function to be used for calculation of the updated deconvoluted signal based on an evaluation value calculated by the convolution error and a magnitude of the variance.

3. The base sequence determination apparatus according to claim 2, wherein the weighting coefficient is used at a time of calculating the evaluation value, to be multiplied to the variance through an input to an interface screen.

4. The base sequence determination apparatus according to claim 3,
wherein a waveform of the updated deconvoluted signal displayed on the interface screen changes depending on a change of an input value of the tolerance.

5. The base sequence determination apparatus according to claim 1,
wherein when calculating the variance of the peak interval of the deconvoluted signal, the processor receives information whether or not to use a calculation result of the variance calculated for a plurality of time segments through a presence or absence of checking on a check column displayed on an interface screen.

6. The base sequence determination apparatus according to claim 1,
wherein the processor corrects a calculation result of the variance of the peak intervals of the deconvoluted signal using a calculation result of the variance calculated for a plurality of time segments other than a time segment corresponding to the calculation result, and specifies the parameter of the point spread function using the corrected variance.

7. The base sequence determination apparatus according to claim 1,
wherein the processor extracts only a parameter candidate, for which a deconvoluted signal satisfying the following (1) to (3) is obtained, before executing the process of specifying the parameter of the point spread function to be used for calculation of the updated deconvoluted signal,
(1) a convolution error between the deconvoluted signal and the mobility correction signal is equal to or less than a predetermined threshold value,
(2) a minimum value of the interval between the peaks extracted from the deconvoluted signal is equal to or greater than a threshold value, and
(3) the parameter candidate of the point spread function exists in the vicinity of an inflection point of the convolution error.

8. The base sequence determination apparatus according to claim 1, wherein
the input device receives an input signal,
the processor obtains a baseline-removed signal from the input signal, and
the processor executes a color conversion process on the baseline-removed signal and calculates the color-converted signal.

* * * * *